United States Patent [19]

Finke et al.

[11] 4,254,271
[45] Mar. 3, 1981

[54] ADDITION OF DIALKYLHALOGENO-HYDRIDOSILANES TO UNSATURATED HYDROCARBON COMPOUNDS

[75] Inventors: Ulrich Finke, Ettlingen; Hans-Heinrich Moretto, Cologne, both of Fed. Rep. of Germany

[73] Assignee: Bayer Aktiengesellschaft, Leverkusen, Fed. Rep. of Germany

[21] Appl. No.: 2,930

[22] Filed: Jan. 12, 1979

[30] Foreign Application Priority Data

Feb. 1, 1978 [DE] Fed. Rep. of Germany ....... 2804204

[51] Int. Cl.³ .............................................. C07F 7/08
[52] U.S. Cl. .................................. 556/479; 556/489; 556/465
[58] Field of Search ................... 260/448.2 E, 448.2 R

[56] References Cited

U.S. PATENT DOCUMENTS

| 2,537,763 | 1/1951 | Hurd | 260/448.2 E |
|---|---|---|---|
| 2,660,597 | 11/1953 | Shafer et al. | 260/448.2 E |

*Primary Examiner*—Paul F. Shaver
*Attorney, Agent, or Firm*—Sprung, Felfe, Horn, Lynch & Kramer

[57] ABSTRACT

In the addition of an unsaturated compound into a silane of the formula $$R_1R_2SiXH$$

wherein
X is Cl or Br, and
$R_1$ and $R_2$ each independently is an alkyl, aryl or aralkyl radical with up to 20 C atoms, or an alkenyl or alkinyl radical with up to 12 C atoms, the improvement which comprises effecting the addition reaction in the presence of at least one of aluminum chloride, aluminum bromide, aluminum oxychloride and aluminum oxybromide.

5 Claims, No Drawings

ADDITION OF DIALKYLHALOGENO-HYDRIDOSILANES TO UNSATURATED HYDROCARBON COMPOUNDS

The present invention relates to a process for the addition of dialkylhalogeno-hydridosilanes, in particular dialkylchloro-hydridosilanes, onto unsaturated hydrocarbons, in particular onto alkenes and alkines, in the presence of catalytic amounts of an aluminum halide or aluminum oxyhalide.

The ability of the Si-H bond to undergo addition reactions with unsaturated hydrocarbons is of particular practical importance for the chemistry of silicones. The reaction opens the path to organo-substituted silanes which are frequently available only with difficulty via other routes, in particular to silanes with a long carbon chain (compare, for example, W. Noll, Chemie und Technologie der Silicone (Chemistry and Technology of the Silicones) (Weinheim 1968) page 45 et seq.).

These addition reactions are catalyzed by the processes customary hitherto, for example by UV light and peroxides. Homopolymerization of the olefin, which competes with the addition reaction, frequently proceeds to a greater or lesser extent as a side reaction.

Noble metals and transition metals or their compounds also catalyze the addition of Si-H compounds onto alkenes and alkines. Examples of such metal compounds are $H_2PtCl_6$; $Pt[P(C_6H_5)_3]_4$; $PtCl2[P(C_6H_5)_3]$; $Ni(C_2H_5)_2(bipy)$, $Ni(acac)_2$ and $Al(C_2H_5)_3$.

The individual reactions can be carried out under various conditions. It is frequently essential to carry out the reaction under pressure or at high temperatures and to accept long reaction times; rearrangement reactions of the reaction products or of the alkenes under such conditions have also be disclosed. The latter case particularly occurs if the alkenes are highly branched.

The present invention relates to a process for the addition of unsaturated compounds with one or more double bonds and/or triple bonds onto silanes of the general formula

$$R_1R_2SiXH$$

wherein
X represents Cl or Br and $R_1$ and $R_2$ are identical or different and represent a straight-chain, branched or cyclic, optionally substituted alkyl radical with 1-20 C atoms, an optionally substituted aralkyl radical or aryl radical with 1-20 C atoms or an alkenyl or alkynyl radical with up to 12 C atoms, the corresponding addition products being formed, characterized in that the addition reaction is carried out in the presence of aluminum chloride, aluminum oxychloride, aluminum bromide and/or aluminum oxybromide.

Surprisingly, it has been found that these reactions proceed extremely easily, with good yields and without substantial formation of rearrangement products.

The catalysts aluminum chloride or aluminum bromide and the corresponding oxyhalides, but preferably $AlCl_3$, can in general be employed in amounts of about 0.01 to 5% by weight, preferably about 0.1-3% by weight, relative to the reaction mixture. However, in order to increase the space/time yields, it is advantageous to increase the catalyst concentration; it is advisable, particularly in the case of a continuous process, to carry out the reaction, for example, in fixed beds consisting of the catalyst, or in reaction vessels which contain relatively large amounts of catalyst.

In general, the temperature during the reaction is adjusted to $-30°$ to $60°$ C., depending on the reactants.

In principle, all dialkylhalogenosilanes can be used as the starting substance for the process according to the invention. Examples of these are: $(CH_3)_2SiHCl$; $(CH_3)(C_2H_5)SiHCl$; and $(C_3H_7)(CH_3)SiHCl$.

Dimethychloro-hydridosilane, a by-product of the direct synthesis (Rochow-Müller process) of methylchlorosilanes, is especially of particular importance in practice.

Unsaturated compounds which are used are, in particular, olefins and acetylenes. The olefins and acetylenes are as a rule those compounds which do not, because of any further functionality, block the catalyst or lead to substantial side reactions with the alkychlorohydridosilane, by themselves or under the action of the catalyst, or prevent the addition reaction.

Examples of suitable compounds with double C-C bonds of triple C-C bonds are: 2-methylbut-2-ene, propylene, cyclohexene, styrene, acetylene, 2,2,4,6,6-pentamethylhept-3ene, α-methylstyrene, hexene, hexine, propine, 1-dodecene, 1-eicosene and 2-methylbut-1-ene. 2-Methylbut-1-ene and 2-methylbut-2-ene, which are both by-products of the direct synthesis (Rochow-Müller process) of methylchlorosilanes, are of particular importance in practice.

The process according to the invention can be carried out with or without a solvent, as desired. Suitable solvents are, for example, saturated hydrocarbon fractions in which the boiling range is not in the boiling range of the product or of any starting component employed in excess which can be recovered.

The process according to the invention is preferably carried out under the pressure of the surrounding atmosphere, because this requires the least effort. However, if desired, higher or lower pressures can also be used. Higher pressures are advantageous, for example, if the alkene or alkine is gaseous.

The conversions achieved in the process according to the invention can reach 80-100 mole per cent, in each case relative to the reactant employed in the lowest amount.

The process can be operated discontinuously or continuously. The latter is particularly preferred in the case of the preparation of olefin-substituted alkylchlorosilanes, in order to prevent any possible diaddition reaction or polymerization. In such a procedure, the olefin-substituted silane is continuously separated off from the reaction mixture.

The reaction times required in the process according to the invention are as a rule short, and are partly determined by the exothermicity of the reaction or of the solubility of the gaseous alkenes or alkines.

The reaction products are worked up by processes which are in themselves customary and known; in general the catalyst is separated off or deactivated and the crude products are separated, for example by distillation, and optionally purified.

Care should also be taken to exclude moisture in the process according to the invention, both in the apparatus and in the solvent, reagent and reactant, as well as in the catalyst.

The fact that no elevated temperature is required, the ready availability of the catalyst and the nature of the products obtained constitute, above all, the advantage of the process according to the invention. The possibility of preparing alkylchlorosilanes with highly branched alkyl radicals is of particular advantage.

The process according to the invention will now be illustrated in more detail with the aid of the examples which follow.

EXAMPLE 1-3 (Comparison example)

The catalysts which follow were added, in each case, to 1 mol of dimethylchlorosilane and 1 mol of 2-methylbut-2-ene (isoamylene) at room temperature, under oxygen and with exclusion of moisture.

Example 1—$H_2PtCl_6$
Example 2—"Lamoraux"-catalyst (compare, for example, DT-AS (German Published Specification) 1,257,752)
Example 3—$Pt[P(C_6H_5)_3]_4$ The catalyst concentration was in each case 100 ppm of platinum, relative to the silane. After stirring for 24 hours, the samples were analyzed. The starting components dimethylchlorosilane and isomylene were present in unchanged form. Hydrosilylation had not occurred.

reflux condenser and dropping funnel or gas inlet tube and 1 g of catalyst was added. Catalyst:
Examples 4–10: $AlCl_3$
Example 11: $Al\ Br_3$
Example 12: Aluminum oxychloride (Al content 21.2%; Cl content 60.7%)

One mol (or a large excess in the case of gases) of the compound to be added on, with a multiple carbon-carbon bond, was added (added dropwise or passed in), while stirring (magnetic stirrer), in a manner such that the reaction temperature did not exceed 10° C. (cooling).

Comparable (and in some cases better) experimental results were obtained when the dimethylchlorosilane and alkene or alkine were added together to a cooled suspension of, for example, cyclohexane/$AlCl_3$.

In the case of some alkenes or alkines, it was sometimes necessary to warm the mixture to about 28°–35° C. at the start of the reaction and to lower the temperature after the start of the reaction.

The results of the procedures are summarized in the table which follows.

| Example No. | Silane | Alkene/alkine | Product | Yield |
|---|---|---|---|---|
| (4) | $(CH_3)_2SiClH$ | 2-methylbut-2-ene (isoamylene) | $H_3C-\underset{\underset{CH_3}{\mid}}{\overset{\overset{H}{\mid}}{C}}-\underset{\underset{H}{\mid}}{\overset{\overset{CH_3}{\mid}}{C}}-\underset{\underset{CH_3}{\mid}}{\overset{\overset{CH_3}{\mid}}{Si}}-Cl$ | 95% |
| (5) | $(CH_3)_2SiClH$ | propene | $CH_3-CH_2-CH_2-\underset{\underset{CH_3}{\mid}}{\overset{\overset{CH_3}{\mid}}{Si}}-Cl$ | 70% |
| (6) | $(CH_3)_2SiClH$ | hex-1-ene | $CH_3(CH_2)_5-\underset{\underset{CH_3}{\mid}}{\overset{\overset{CH_3}{\mid}}{Si}}-Cl$ | 81% |
| (7) | $(CH_3)_2SiClH$ | acetylene | $H_2C=C\underset{\underset{CH_3}{\mid}}{\overset{\overset{H}{\diagup}}{\underset{\diagdown}{CH_3}}}\underset{\underset{CH_3}{\mid}}{\overset{}{Si}}-Cl$ | 70% |
| (8) | $(CH_3)_2SiClH$ | cyclohexene | cyclohexyl(H)–$\underset{\underset{CH_3}{\mid}}{\overset{\overset{CH_3}{\mid}}{Si}}$–Cl | 72% |
| (9) | $(CH_3)_2SiClH$ | styrene | $C_6H_5-CH_2-CH_2-\underset{\underset{CH_3}{\mid}}{\overset{\overset{CH_3}{\mid}}{Si}}-Cl$ | 80% |
| (10) | $(CH_3)_2SiClH$ | α-methylstyrene | $C_6H_5-\underset{\underset{H}{\mid}}{\overset{\overset{CH_3}{\mid}}{C}}-CH_2-\underset{\underset{CH_3}{\mid}}{\overset{\overset{CH_3}{\mid}}{Si}}-Cl$ | 85% |
| (11) | $(CH_3)_2SiClH$ | 2-methylbut-2-ene | $H_3C-\underset{\underset{H}{\mid}}{\overset{\overset{CH_3}{\mid}}{C}}-\underset{\underset{CH_3}{\mid}}{\overset{\overset{H}{\mid}}{C}}-\underset{\underset{CH_3}{\mid}}{\overset{\overset{CH_3}{\mid}}{Si}}-Cl$ | 90% |
| (12) | $(CH_3)_2SiClH$ | 2-methylbut-2-ene | $H_3C-\underset{\underset{H}{\mid}}{\overset{\overset{CH_3}{\mid}}{C}}-\underset{\underset{CH_3}{\mid}}{\overset{\overset{H}{\mid}}{C}}-\underset{\underset{CH_3}{\mid}}{\overset{\overset{CH_3}{\mid}}{Si}}-Cl$ | 80% |

EXAMPLE 4-12

General instructions 1 mol of dimethylchlorosilane was cooled to 5° C. in a 0.5 l three-necked flask with an internal thermometer, The physical data of the products 5–10 are identical to the data in the literature.

The reaction product of Example 4, 1,2-dimethylpropyl-1-dimethylchlorosilane, boiling point $_{760}153°$ C.; D-0.9; $N_D^{20}$ 1.4360, was prepared for the first time; its structure could be confirmed by $^1$H- and $^{13}$C-NMR spectroscopy. It is particularly suitable for the silylation of, for example, alcohols or organic acids, the silyl ethers or silyl esters formed having increased stability to hydrolysis and lipophilic character.

It will be appreciated that the instant specification and examples are set forth by way of illustration and not limitation, and that various modifications and changes may be made without departing from the spirit and scope of the present invention.

What is claimed is:

1. In the addition of an unsaturated compound onto a silane of the formula $$R_1R_2SiXH$$

wherein

X is Cl or Br, and $R_1$ and $R_2$ each independently is an alkyl, aryl or aralkyl radical with up to 20 C atoms, or an alkenyl or alkinyl radical with up to 12 C atoms, the improvement which comprises effecting the addition reaction in the presence of at least one of aluminum chloride, aluminum bromide, aluminum oxychloride and aluminum oxybromide.

2. A process according to claim 1, wherein the silane is dimethylchlorosilane.

3. A process according to claim 1, wherein the unsaturated compound is at least one of 2-methylbut-1-ene and 2-methylbut-2-ene.

4. A process according to claim 3, wherein the silane is dimethylchlorosilane, the temperature is between about −30° and 60° C., and the aluminum compound is aluminum chloride present in about 0.01 to 5% by weight of the reaction mixture.

5. 1,2-dimethylpropyl-1-dimethylchlorosilane.

* * * * *